United States Patent [19]

Self

[11] Patent Number: 4,828,985
[45] Date of Patent: May 9, 1989

[54] ANTIBODIES AGAINST THE COMPLEX OF A SMALL MOLECULE AND ITS BINDING PROTEIN, THEIR PREPARATION AND THEIR USE IN DIAGNOSTIC METHODS

[75] Inventor: Colin H. Self, Ealing, United Kingdom

[73] Assignee: Cambridge Patent Developments Limited, England

[21] Appl. No.: 832,710

[22] PCT Filed: Jun. 11, 1985

[86] PCT No.: PCT/GB85/00255
§ 371 Date: Feb. 7, 1986
§ 102(e) Date: Feb. 7, 1986

[87] PCT Pub. No.: WO86/00140
PCT Pub. Date: Jan. 3, 1986

[30] Foreign Application Priority Data

Jun. 12, 1984 [GB] United Kingdom ............... 8414901

[51] Int. Cl.$^4$ ............................................. G01N 33/53
[52] U.S. Cl. ........................................ 435/7; 435/21; 435/810; 436/506; 436/507; 436/513; 436/518; 436/547; 436/805; 436/808; 530/387
[58] Field of Search ............................ 435/7, 21, 810; 436/506, 507, 513, 518, 547, 805, 808; 530/387

[56] References Cited

U.S. PATENT DOCUMENTS

| 4,132,767 | 1/1979 | Tohmatsu et al. ................. 530/387 |
| 4,544,640 | 10/1985 | Soma et al. ........................ 436/507 |
| 4,670,383 | 6/1987 | Baier ..................................... 435/7 |

FOREIGN PATENT DOCUMENTS

| 0091760 | 10/1983 | European Pat. Off. . |
| 8602736 | 5/1986 | PCT Int'l Appl. ................. 435/7 |
| 1587193 | 1/1981 | United Kingdom . |

OTHER PUBLICATIONS

International Search Report, Nemazee, D. et al: "Enchancing Antibody: A Novel Component of the Immune Response", pp. 3828–3822.
Chemical Abstract, vol. 92, No. 9, 3 Mar. 1980, p. 483, Abstract 74158d.
Chemical Abstract, vol. 83, No. 1, 7 Jul. 1975, p. 600, Abstract 69335.
Chemical Abstract, vol. 95, No. 1, 6 Jul. 1981, p. 487, Abstract 49285.

Primary Examiner—Robert J. Warden
Assistant Examiner—Robert Benson
Attorney, Agent, or Firm—Jacobs & Jacobs

[57] ABSTRACT

The invention involves polyclonal antibodies reactive with a complex of a hapten and its binding protein, wherein the antibodies are unreactive with the free hapten or free binding protein. The antibodies are useful in assays of the hapten or the binding protein.

21 Claims, No Drawings

ANTIBODIES AGAINST THE COMPLEX OF A SMALL MOLECULE AND ITS BINDING PROTEIN, THEIR PREPARATION AND THEIR USE IN DIAGNOSTIC METHODS

The present invention relates to a class of polyclonal antibodies, which may be free or present in a complex, to the preparation of such antibodies and to their use in reactions which employ antibody-antigen interactions.

Reactions between an antigen and its antibody have found many applications in biotechnology and especially in diagnostic tests, for example medical (including veterinary) diagnostic tests, gene probes, and the like. Recently the art has moved forward rapidly due in large part to the introduction of monoclonal antibodies which allow great specificity and accuracy (for a discussion of monoclonal antibodies see for example G. Galfre and C. Milstein, Methods in Enzymology, 73, 3-57, 1981).

A monoclonal antibody was described by D. A. Nemazee and V. J. Sato (see Proc. Natl. Acad. Sci USA, V2, 79, pp 3828-3832, 1982) which was an antibody against a complex of two other antibodies as a result of exposing a new epitope in the Fc region of one of the original antibodies. Since the original antibodies were both macromolecules conformational changes in the Fc region was not unexpected. Similar changes would not be expected to occur if a small molecule had been employed. Similarly since small molecules cannot have simultaneous multiple epitopes and cannot thus themselves bind more than one antibody, (for example see R. J. Thompson and A. P. Jackson, TIBS, 9, pp 1-3, 1984) the effect described by Nemazee and Sato would not be expected if a complex employing a small molecule was used.

I have now discovered that, if the normal tendency to use monoclonals is reversed, certain new polyclonal antibodies may be produced by a simple process and be used in reactions which employ antibody-antigen interactions. I have found that if certain polyclonal antibodies are made free of certain other antibodies, then they are of use in, inter alia, diagnostic tests and are particularly advantageous in such tests if they are labelled.

Accordingly the present invention provides a polyclonal antibody characterised in that said polyclonal antibody is a secondary polyclonal antibody against a complex of a non-immunogenic molecule and a binding protein against said non-immunogenic molecule which secondary antibody is free from antibodies againt the non-immunogenic molecule and against its binding protein.

The non-immunogenic molecule is normally a small molecule, that is a molecule of molecular weight less than 5000. Such small molecules more aptly have a molecular weight of less than 2000 and favourably have a molecular weight of less than 1200.

The skilled art worker will appreciate that low molecular weight materials are normally non-immunogenic but that antibodies thereto can be obtained by immunising an animal with a conjugate of the non-immunogenic molecule (or a very close analogue) with an immunogenic material such as bovine serum albumin or an equivalent agent. The desired antibody may then be obtained by methods known per se.

Proteins used in this invention may be antibodies or other proteinaceous materials such as enzymes, binding proteins such as steroid binding proteins or vitamin binding proteins. Preferably the protein used in this invention is an antibody in which case the small molecule may be termed herein a small antigen.

Thus in a favoured aspect the present invention provides a secondary polyclonal antibody against a complex of a non-immunogenic molecule and a primary antibody against said non-immunogenic molecule said secondary polyclonal antibody being free from antibodies against the non-immunogenic molecule and its primary antibody.

Herein the term "primary antibody" refers to an antibody which will bind the non-immunogenic molecule per se. This primary antibody may be a polyclonal antibody or a monoclonal antibody. It is desirable to employ a polyclonal antibody because they are more readily available and surprisingly it has been found to be effective when producing the secondary antibody of this invention. It is also sometimes desirable to employ a monoclonal primary antibody since, although more difficult to make, a more specific product can be obtained. Herein the term "non-immunogenic" molecule means one which when injected into an animal does not cause that animal to produce antibodies thereto. The skilled art worker will appreciate that normally such non-immunogenic molecules are low molecular weight materials (normally less than 1200) but that antibodies thereto can be obtained by immunising an animal with a conjugate of the non-immunogenic molecule and an immunogenic material such as bovine serum albumin or equivalent agent. The animal produces an array of antibodies some of which are against the non-immunogenic molecule per se. If desired some or all of the antibodies against the immunogenic carrier employed in making the conjugate (such as bovine serum albumin) may be removed from the array by absorption with an appropriate immunoabsorbent.

Happily it has been found that when producing a polyclonal secondary antibody it is not necessary to employ "unnatural" materials such as the arsenic containing material employed by Nemazee and Sato but that organic molecules free of metallic elements can also be employed. In fact, advantages accrue when the non-immunogenic molecule employed is free of metallic elements such as arsenic.

Herein the term "secondary polyclonal antibody" means a polyclonal antibody which is an antibody against a complex of a non-immunogenic molecule and a primary antibody against said non-immunogenic molecule but which is not an antibody against the non-immunogenic molecule or against the primary antibody against said non-immunogenic molecule. The ratio of equilibrium constants between (a) the secondary polyclonal antibody and the complex and (b) the secondary polyclonal antibody and either component of the complex should be greater than 100:1, more suitably greater than 1000:1 and preferably greater than 10,000:1.

The antibody may be the complete immunoglobulin or fragment thereof having the described binding activity. As will become apparent hereinafter, certain embodiments of this invention will benefit more from the use of the complete immunoglobulin than from a fragment thereof whereas other embodiments will benefit more from the use of fragments of the complete immunoglobulin such as the Fab and F(ab')$_2$ fragments. This reflects the view that the binding between the secondary antibody and the complex takes place at or about the site of binding of the small molecule.

The secondary polyclonal antibody of this invention is most suitably one against a complex wherein the non-immunogenic molecule has a molecular weight of 200 to 1000, more aptly 250 to 750 and preferably 300 to 600, especially when said non-immunogenic molecule is free of metallic elements.

A favoured use of the secondary antibodies of this invention is in diagnostic tests. Reduction in reversibility in reactions can lead to higher apparent affinity between ligand and antiligand which can lead to improved stability of washing, faster reaction times and the like. Also use of a secondary polyclonal antibody of this invention can allow small molecules to be determined by non-competitive methods such as Sandwich methods which can operate over a wider range of concentrations and can be less sensitive to the nature and mode of use of the reagents. This will be apparent hereinafter.

In one highly favoured form the secondary polyclonal antibody of this invention is one against a complex wherein the non-immunogenic molecule is one which occurs naturally in humans, for example a hormone (such as a steroid hormone such as estradiol, testosterone, progesterone, hydrocortisone, cortisone, estratriol, estrogen and androstandiol) or a vitamin, peptide or saccharide or the like, or is one which is administered to humans such as a medicament (such as antibiotic, mood modifier, analgesic or cardioactives such as digoxin) or drug of abuse (such as morphine, methadone, cannabiniol, cocaine alkaloids or the like).

From the foregoing it will be appreciated that in one particularly apt aspect this invention provides a polyclonal antibody against a complex of a non-immunogenic hormone and an antibody to said hormones which antibody is not an antibody against the hormone or against the said antibody to said hormone.

Similarly it will be appreciated that in another particularly apt aspect this invention provides a polyclonal antibody against a complex of a non-immunogenic drug and an antibody to said drug which antibody is not an antibody against the drug or against said antibody to said drug. Suitably the drug is a medicament, for example as hereinbefore indicated. Suitably the drug is a drug of abuse as hereinbefore indicated.

The antibody to the hormone or drug etc. may be a monoclonal or polyclonal antibody of which I prefer to employ a monoclonal antibody.

The secondary polyclonal antibodies of this invention are particularly useful in diagnostic tests for the non-immunogenic molecule. Diagnostic tests for such molecules employing immunological reactions are notoriously difficult and hitherto have not been practicable if the two-site approach is employed. Whereas an unlabelled secondary polyclonal antibody may be employed when the complex is labelled or when a precipitation reaction is used, it has been found to be highly desirable to label the secondary polyclonal antibody with a label that allows its detection.

Accordingly, in one highly favoured aspect, this invention provides a secondary polyclonal antibody against a complex of non-immunogenic molecule and a primary antibody against said non-immunogenic molecule said polyclonal antibody being free of antibodies against the non-immunogenic molecule and its primary antibody, said secondary polyclonal antibody being labelled whereby it is detectable.

The label employed may be introduced into the secondary polyclonal antibody in any suitable manner which does not prevent the secondary polyclonal antibody acting as such. The label may be isotopic or non-isotopic. Isotopic labels may employ an convenient isotope which is normally and preferably introduced to the secondary polyclonal antibody after its formation. Although isotopic labelling can yield very readily detectable materials it necessitates the use of complex equipment and the careful handling associated with radioactive materials. Because of this I prefer to employ non-isotopic methods of labelling.

Any convenient method of non-isotopic labelling may be employed. Methods of labelling antibodies with materials which render them detectable are widespread and well understood by the skilled art worker, for example a method set forth by P. R. Raggett and C. N. Hales in "Immunoassays using labelled antigens or antibodies" in Clinical Aspects of Immunology, Ed. Peters and Lackman, Blackwell Scientif Publications, Oxford, 1983. However, the two methods I prefer to employ are (a) to label the secondary polyclonal antibody with an enzymatic label and (b) to label the secondary antibody with a luminescent moiety (such as a bioluminescent, chemiluminescent, or fluorescent material).

Labelling the secondary polyclonal antibody with an enzyme such as phosphatase or peroxidase allows detection by allowing the enzyme to express its activity. Favoured enzyme labels include phosphatase, peroxidase $\beta$-galactosidase, lysozyme and dehydrogenases such as malate or glucose-6-phosphate dehydrogase. Phosphatases may be observed by their ability to dephosphorylate compounds to yield materials which are detected. Peroxidase may be observed by their ability to give rise to hydrogen peroxide which may be detected. $\beta$-Galactosidase may be observed by their ability to hydrolyse $\beta$-galactosides to give rise to detectable products. Lysozyme may be observed by their ability to rupture bacterial cells which can give rise to turbidity changes. Dehydrogenases may be observed by its ability to give rise to the change in the oxidative state of NAD and NADH. Many methods of labelling with such enzymes will occur to the skilled art worker but the method I prefer to use is to covalently link the enzyme to the secondary polyclonal antibody by reacting with a bifunctional organic compound such as a dialdehyde, for example glutaraldehyde. Many methods of detecting phosphatases, peroxidase (or any suitable enzyme) will be known to the skilled art worker but I prefer to detect the labelled antibody by allowing a phosphatase to dephosphorylate a phosphate. Either the dephosphorylated compound may be detected directly (for example when p-nitrophenyl phosphate is dephosphorylated to p-nitrophenyl) or indirectly for example when NADP is dephosphorylated to NAD to start a cyclic chemical reaction which amplifies the effect). Favoured enzyme labels include acid and alkaline phosphatases. A preferred enzyme label is alkaline phosphatase.

The labelled secondary polyclonal antibody of this invention may be employed in enzyme immunoassays (including ELISA systems) in analogous manner to the use of primary antibodies for the detection of high molecular weight antigens even though the material to be detected in the method of this invention is a non-immunogenic molecule.

In two site assays two recognition sites are necessarily involved in the detection of a material. A convenient method for carrying out two site assays is by bonding onto a surface an antibody reactive with one site on the material, exposing it to the material and exposing the material thus held on the surface to another, labelled, antibody reactive with a second site on the material. Unless the material has multiple copies of the same site per molecule, it has been necessary to use antibodies against distinct and separate sites, and even in those cases where multiple copies exist on the molecule it is better to have the bound and labelled antibodies specific for distinct and separate sites to reduce the possibility of competition for individual sites. With large immunogenic molecules it is usually possible to produce antibodies against two distinct and separate sites. For small molecules, however, this is not the case. The method of this invention overcomes this problem. For example, a two site assay may be constructed for a small molecule by binding the first (primary) antibody to a surface, exposing the material to be detected then to a labelled secondary polyclonal antibody specific for a second site formed by the association of the first antibody and the material to be detected.

Antibody-antigen precipitation reactions dependent on matrix formation as a result of multi-valent interactions of antibody and antigen (for example as described in L. Hudson & F. C. Hay, Practical Immunology, Chapter 5, Published by Blackwell Scientific Publications (1981)) may benefit from the development of secondary polyclonal antibodies. Small molecules do not normally precipitate with primary antibody as they can only bind one primary antibody molecule at a time, however, in the presence of polyclonal secondary antibody chains and matrices of such small molecules an antibody may be formed leading to precipitation and indicating the presence of the small molecule.

The present invention provides a process for preparing a secondary polyclonal antibody of this invention which method comprises immunising an animal with a complex of a non-immunogenic molecule and its primary antibody to yield an antiserum containing said secondary polyclonal antibody, obtaining the desired secondary polyclonal antibody from said antiserum and obtaining said polyclonal antibody free from antibodies against the non-immunogenic molecule and its primary antibody; and thereafter if desired labelling said polyclonal antibody with a label which renders it detectable. Analogous methods may be employed to form antibodies wherein the complex is of a non-immunogenic molecule and binding proteins other than antibodies.

Each of the individual steps in this process may be performed by methods known to the skilled art worker. However, as will be readily appreciated the skilled art worker heretobefore had no reason to combine the necessary steps in the specified manner. The process of this invention in many ways is much easier to carry out than processes in preparing analogous monoclonal antibodies.

The process of this invention will naturally be adapted to the preparation of preferred secondary polyclonal antibodies as hereinbefore indicated.

The immunisation of an animal with a complex of a non-immunogenic molecule with its binding protein can give rise to antibodies to the binding protein itself. These should be removed by for example exposure of the antiserum to binding protein immobilised on a surface.

Since in a favoured form the binding protein to the small molecule is an antibody (aptly a monoclonal antibody), in a further aspect the present invention provides a method of determining a member of a non-immunogenic molecule primary antibody pair which method comprises contacting a suspected source of a member of the pair with another member of the pair and with a secondary polyclonal antibody to the complex of the pair which is not an antibody to the non-immunogenic molecule or its primary antibody and measuring the association between the complex and the secondary polyclonal antibody.

The measurement of the association between the member of the pair to be determined and the other member of the pair or the secondary polyclonal antibody may be qualitative or quantitative but is most beneficially quantitative. Any suitable method may be employed which will measure the binding of an antibody to its antigen, for example by immobilising one component on a solid substrate and measuring the amount of the other component which becomes bound to the solid substrate; or by binding one component to an enzyme which enzyme's activity is altered when another component binds to the first component; or agglutination; or by precipitation.

As previously indicated the member of the pair added to the reaction or the secondary polyclonal antibody may be labelled with a signal generating means. This signal generating means can be employed to measure the association of the materials.

Since it is preferred to employ a secondary polyclonal antibody which is labelled with signal generating means in a favoured aspect a method of determining a member of a small molecule antibody pair which method comprises contacting a suspected source of the member of the pair with the other member of the pair and with a secondary polyclonal antibody to the complex of the pair which secondary polyclonal antibody is labelled with signal generating means and measuring the association between the member of the pair to be determined and the secondary polyclonal antibody which measurement employs the signal generating means. (The antibody in the compex is favourably a monoclonal antibody).

The determination method of this invention may be adapted to the determination of the small molecule or its antibody. However, the method of this invention is most favourably adapted to the determination of a small molecule (i.e. a non-immunogenic molecule).

Thus in a favoured aspect the present invention provides a method of determining a small molecule which method comprises contacting a suspected source of the small molecule with a primary antibody to said small molecule and with a secondary polyclonal antibody to the complex of said small molecule and primary antibody and measuring the association between the complex and secondary antibody. (The primary antibody is aptly a monoclonal antibody).

The measurement of the association is most aptly carried out employing a signal generation means with which either the primary or secondary polyclonal antibody os labelled. However, as previously indicated it is preferred to employ a secondary polyclonal antibody which is labelled with a signal generation means.

Thus in a preferred aspect, the present invention provides a method of determining a small molecule which method comprises contacting a suspected source of said small molecule with a primary antibody (preferably monoclonal) to said small molecule with a secondary polyclonal antibody to the complex of the small molecule and its primary polyclonal antibody which secondary polyclonal anitbody is labelled with signal generating means and measuring the association between the complex and the secondary polyclonal antibody which measurement employs the signal generating means.

The source of the material to be determined is normally a biologically derived fluid such as blood, serum, plasma, urine, milk, saliva or tissue extracts or fluid materials derived from the food industry. Thus for example diagnostic tests may be carried out for the materials hereinbefore described using the appropriate secondary antibody.

In one particularly apt form of this invention a member of the small molecule primary antibody pair is bound to a surface, a suspected source of the other member of the pair is brought into contact with the surface and the secondary polyclonal antibody labelled with signal generating means is also brought into contact with the surface, the system is incubated until the other member of the pair and the secondary polyclonal antibody become bound to the first member of the pair and hence to the surface, the liquid is separated from the surface and the signal generating means is employed to measure the secondary polyclonal antibody thereby determining the amount bound and hence the amount of the member of the pair to be determined.

Normally and preferably the secondary polyclonal antibody which is measured is that fraction which becomes bound to the surface (as opposed to measuring the amount remaining in solution which is a less suitable method).

Most suitably this aspect of the invention is adapted to determine a small molecule so that the member of the pair to be bound to the surface is the primary antibody (which is aptly a monoclonal antibody).

Thus in a highly favoured form this invention provides a method of determining a small molecule in a source suspected of containing it which comprises binding a primary antibody (generally a monoclonal antibody) to said small molecule to a surface, contacting the thus bound primary antibody with the suspected source of small molecule and with a secondary polyclonal antibody labelled with signal generating means, incubating the system until small molecule and secondary polyclonal antibody become bound to the primary antibody and hence to the surface, separating the liquid from the surface and determining the secondary polyclonal antibody on the surface by employing the signal generating means.

In an alternative apt form of this invention a secondary polyclonal antibody to a complex of a small molecule and a primary antibody (generally a monoclonal antibody) one of which is labelled with a signal generating means is bound to the surface, a suspected source of one member of the complex is brought into contact with the surface and the other member of the complex is brought into contact with the surface, the sysstem is incubated until complex is formed and becomes bound to the secondary polyclonal antibody and hence to the surface, the liquid is separated from the surface and the signal generating means is employed to measure the complex bound and hence the amount of the member of the complex to be determined.

Normally and preferably that fraction of the complex which is measured is that fraction which becomes bound to the surface (as opposed to measuring the amount remaining in solution which is a less suitable method).

Preferably the preceding method is adapted to the determination of the small molecule so that the primary antibody is labelled with the signal generating means.

Thus in a favoured form, this invention provides a method of determining a small molecule in a source suspected of containing it which comprises binding a secondary polyclonal antibody to a surface which secondary polyclonal antibody is one against a complex of the antigen and a primary antibody (generally monoclonal) labelled with signal generating means, contacting the thus bound secondary polyclonal antibody with the suspected source of small molecule and with labelled primary antibody, incubating the system until antigen and labelled primary antibody become bound to the secondary polyclonal antibody, separating the liquid from the surface and determining the primary antibody on the surface by employing the signal generating means and hence determining the small molecule.

Although these methods of the invention employing surfaces offer advantages for molecules in the 1200–5000 molecular weight range the advantages are particularly marked when employed in the determination of small antigens below 1200 (since small antigens could not hitherto be readily determined by ELISA or analogous assays).

In yet another aspect, this invention provides a method of determining a small molecule antibody pair (in which the antibody is aptly monoclonal) which method comprises binding one of the pair to a surface and contacting that surface with a suspected source of the other member of the pair, a secondary polyclonal antibody to the complex of the pair and the other member of the pair labelled with signal generating means, incubating the system, separate the liquid from the surface and measuring the association between the labelled component and the surface and thereby determining the abount of substance to be determined present in the source suspected of containing it. Normally this involves comparing the amount of labelled component which becomes bound to the amount which becomes bound in the presence of known amounts of the unlabelled material to be determined.

Normally it is preferred to adapt this method to the detection of a small molecule in which case the primary antibody is bound to the surface. Preferably the retained label bound to the surface is determined (as opposed to the fraction remaining in solution).

The secondary polyclonal antibodies of this invention may also be employed in diagnostic tests employing agglutination.

In one suitable aspect the present invention provides a method of determining a small molecule which method comprises binding the small molecule to solid particles, contacting said small molecule bound particles with a suspected source of small molecule and with a secondary polyclonal antibody to a complex of small molecule and a primary antibody (generally monoclonal) thereto and measuring the resulting agglutination. If antigen is present in the source a reduction in the amount of agglutination occurs which may be used to indicate the amount of small molecule in the source.

In a further favoured agglutination test, a primary antibody is bound to particles and contacted with the secondary polyclonal antibody and a suspected source of small molecule. In such a test the amount of agglutination is indicative of the amount of small molecule in the test sample.

The determinations of this invention will normally be performed under conventional conditions for such determinations, for example at a temperature of 4°–45° C., more usually 15°–38° C. and preferably at 18°–25° C.; in aqueous solutions which are generally substantially isotonic; and at a pH of 2–10, more usually 5–9, preferably 6–8 and most preferably at about 7.

The secondary polyclonal antibodies of this invention may be made by forming a complex between a small molecule and its antibody (usually monoclonal) (or other binding protein) the complex is then used as an immunogen to raise polyclonal antibodies by methods known per se.

This invention with respect to diagnostic methods also extends to determinations of small molecules which form complexes with binding proteins in analogous manner to the hereinbefore described methods employing small molecules and their antibodies.

Most aptly the small molecules employed in or determined by a method of this invention are those which are soluble in water since this eases complex formation. Such molecules generally have hydroxyl, amino or carboxyl groups. Complexes (for immunisation) may be prepared by dissolving or intimately dispersing the small molecule and binding protein together in aqueous media which may contain a surfactant. Often a large excess of the small molecule is employed. The complexes may be injected in solution optionally together with an adjuvent such as complete or incomplete Freunds adjuvant. The complexes may also be employed in precipitated form.

The present invention also extends to diagnostic kits which incorporate a secondary polyclonal antibody of this invention. Preferred kits will comprise a labelled secondary polyclonal antibody of this invention. Most aptly the kits of this invention will comprise an antibody of this invention in the form of a solid (e.g. in a bottle) or absorbed into or onto a solid surface e.g. a well on a plate). Freeze dried materials are apt.

In one method of this invention primary antibody may be on the surface of a well or other isolating surface, the solution to be determined is contacted with that surface for sufficient time for small molecule to become bound to the surface, optionally the solution is removed from the surface, labelled secondary antibody is introduced and the solution incubated. The solution is separated from the solid surface which is then washed and the bound label determined. In an alternative method the solution to be determined and the secondary antibody are added at essentially the same time. In yet another method the labelled secondary antibody is present before the introduction of the solution to be determined.

In analogous manner labelled primary antibody may be employed.

Complexes of a small molecule and a primary antibody (generally a monoclonal antibody) may be rendered more immunogenic if the primary antibody is first conjugated with an antigenic material such as alkaline phosphatase. Thus in a preferred form the complex used to raise the secondary polyclonal antibody is a complex including a primary antibody conjugated with an antigenic material such as alkaline phosphatase. (Antibody against the antigenic material may be later removed using an immunoabsorbent).

The following Examples illustrate the invention:

EXAMPLE 1

Development of Secondary Antibodies Against Testosterone-Primary Antibody Testosterone Complex Rabbit anti-testosterone antiserum is made by immunising rabbits with Testosterone 3-CMO-BSA. The IgG fraction is made and purified by conventional methodology (fraction-A). A solution of 40 mg of this in 1 ml isotonic phosphate buffered saline at pH7.4 is mixed with 100 ug of testosterone (Sigma-T 1500 together with surfactant). It is gently mixed at room temperature for one hour and left overnight at 4° C. The mixture is then used to immunise two rabbits after which antiserum is collected and IgG fractions isolated (fraction-B). An immunoabsorbent column is then made to remove from the fraction-B any IgG antibody which might be reactive with only the primary antibody as follows: 20 g of cyanogen bromide activated Sepharaose 4B (Sigma-C 9142 is swollen in 150 ml of borate saline buffer pH 8.4, ionic strength 0.1 and 200 mg of IgG fraction-A (above) in 50 ml borate sale buffer added and mixed for four hours at room temperature. The unbound IgG is washed away with phosphate buffered saline and the sepharose immunoabsorbent poured into a glass container to form an immunoabsorbent column. Through this is passed 10 mg of fraction-B in 10 ml phosphate buffered saline over one hour at 4° C. The purified material in the eluant is collected.

Determination of Testosterone Using Secondary Antibody

Five mg of immunoabsorbed fraction-B is conjugated to calf intestinal alkaline phosphatase (Sigma-P 9517) with glutaraldehyde by the method described by E. Engvall and P. Perlmann (1971) in Immunochemistry, 8, 871.

The wells of a (Nunc) microtitre plate are layered with fraction-A by putting in each well 200 μl of a 1 ng to 100 ng per ml of fraction-A in a 20 mM carbonate bicarbonate buffer at pH 9.6 and leaving it at 37° C. for one hour followed by removal of the solution, replacement with a 0.2% lactalbumin (Sigma 1 L 5385) solution and leaving overnight at 4° C. The lactalbumin is then discarded and the wells washed four times with Tris-buffered saline containing 0.02% Tween 20. 100 μl of solutions containing 10 ng, 1 ng, 0.1 ng, 10 pg, 1 pg, 0.1 pg, 10 fg and 0 of testosterone are added in to six rows of duplicate wells followed by 100 μl of the following dilutions of alkaline phosphatase conjugated fraction-B to each duplicate row: 100 ng/ml; 10 ng/ml; 1 ng/ml; 0.1 ng/ml; 10 pg/ml; 1 pg/ml. The mixtures are incubated overnight at room temperature, after which the solutions are discarded and the wells washed four times with Tris-buffered saline pH 7.4. The remaining alkaline phosphatase is assayed by adding 200 μl of diethanolamine buffer at pH 10.3 containing 10 mM p-nitro-phenyl phosphate and 3.3 mM MgCl2 to each well and measuring the absorbance change at 405 nm.

The method is shown to detect the presence of testosterone and a suitable concentration of conjugate is chosen to provide good sensitivity with low background interference for further use.

EXAMPLE 2

Development of Secondary Antibodies Against Hydrocortisone-Primary Antibody Hydrocortisone Complex Rabbit anti-hydrocortisone antiserum is made by immunising rabbits with Cortisol-21-HS-Thyroglobulin. The IgG fraction is made and purified by conventional methodology (fraction-A). A solution of 50 mg of this in 1 ml phosphate buffered saline at pH 7.4 is mixed with 100 μg of hydrocortisone (Sigma-H 4001). This is gently mixed at room temperature for one hour and left overnight at 4° C. The mixture is then used to immunise two rabbits after which the IgG fraction is isolated from their antiserum (fraction-B). An immunoabsorbent column is then made to remove from the fraction-B any IgG antibody which might be reactive with only the primary antibody as follows: 20 g of cyanogen bromide activated Sepharose 4B (Sigma-C 9142) is swollen in 150 ml of borate saline buffer and 200 mg of IgG fraction-A (above) in 50 ml borate saline buffer added and mixed for four hours at room temperature. The unbound IgG is washed away with phosphate buffered saline and the sepharose immonoabsorbent poured into a glass container to form an immunoabsorbent column. Through this is passed 10 mg of fraction-B in 10 ml phosphate buffered saline over one hour at 4° C. The purified material in the eluant is collected.

Precipitation Test for Secondary Antibody

In a small rimless (Durham) test tube is placed 0.2 ml of a phosphate buffered saline containing 2 mg fraction-A mixed with 400 ng hydrocortisone and 5% sucrose. On top of this is carefully layered 0.2 ml of a phosphate buffered saline containing 2 g of immunoabsorbed fraction-B. Precipitation shows the presence of secondary antibodies and may itself be used to demonstrate the presence of the hydrocortisone. This is shown by the absence of precipitation in a control carried out in the absence of the small molecule.

Determination of Hydrocortisone Using Secondary Antibody

Five mg of immunoabsorbed fraction-B is conjugated to calf intestinal alkaline phosphatase (Sigma—P 9517) with glutaraldehyde by the method described by E. Engvall and P. Perlmann (1971) in Immunochemistry, 8, 871.

The wells of a (Nunc) microtitre plate are layered with fraction-A by putting in each well 200 μl of a 1 ng per ml solution of fraction-A in 20 mM carbonate bicarbonate buffer at pH 9.6 and leaving it at 37° C. for one hour followed by removal of the solution, replacement with a 0.2% lactalbumin solution and leaving overnight at 4° C. The lactalbumin is then discarded and the wells washed four times with Tris-buffered saline containing 0.02% Tween 20. 100 μl of solutions containing 10 ng, 0.1 ng, 1 pg, 0.1 pg, 10 fg and 0 of hydrocortisone are added in to six rows of duplicate wells followed by 100 μl of the following dilutions of alkaline phosphatase conjugated fraction-B to each duplicate row: 100 ng/ml; 10 ng/ml; 1 ng/ml; 0.1 ng/ml; 10 pg/ml; 1 pg/ml. The mixtures are incubated overnight at room temperature, after which the solutions are discarded and the wells washed four times with Tris-buffered saline pH 7.4. The remaining alkaline phosphatase is assayed by conventional method. For example, addition of 10 mM p-nitrophenyl phosphate in 200 μl diethanolamine buffer at pH 10.3 containing 3.3 mM MgC12 and measurement of the absorbance change at 405 nm.

The method is shown to detect the presence of hydrocortisone and a suitable concentration of conjugate is chosen to provide good sensitivity with low background interference.

EXAMPLE 3

Example 1 is repeated using a monoclonal antibody against testosterone.

EXAMPLE 4

Example 2 is repeated using a monoclonal antibody against hydrocortisone.

EXAMPLE 5

Determination of Proproanolol

Rabbit anti-propranolol antiserum is made and purified by conventional technology by immunising animals with a propranolol-bovine serum albumin conjugate made with N-(4-bromobutyl)phthalimate (Sigma Chemical Co. London Ltd. catalogue number B 3502) by conventional means. The IgC fraction of this is made and purified by conventional means (Fraction M). A solution of 50 mg of this in 1 ml phosphate buffered saline at pH 7.4 is mixed with 100 μg of propanolol (Sigma cat no. P 0884). This is gently mixed at room temperature and left at 4° C. overnight. The mixture is then used to immunise a sheep after which the IgG fraction is isolated from its antiserum (Fraction N). An immunoabsorbent column is then made to remove from Fraction N any antibody which might be reactive with only the primary antibody, as follows: 200 mg of IgG fraction M is made into an immunoabsorbent using Sera-Lab Insolumer kits according to the manufacturer's instructions. 50 mg of fraction N is exposed to this in 5 ml of 50 mM Tris buffer at pH 7.4 containing normal saline and gently mixed for one hour at room temperature. The supernatant is then obtained by centrifugation and subsequent filtration. Four mg of this material is then conjugated to calf intestinal alkaline phosphatase (Sigma—P 9517) with glutaraldehyde by the method of Engvall and Perlmann.

Into each well of a Nunc microtitre plate is put 200 μl of a 50 ng/ml solution of fraction M in 40 mM bicarbonate buffer at pH 916. The solutions are left for four hours at room temperature, then shaken out and replaced with 0.2% ovalbumin in the same buffer which is left overnight at 4° C. This is then shaken out and the wells washed four times with Tris buffered saline containing 0.02% Tween 20. 100 μl of solutions containing a range of concentration of propranolol from 1 mg/ml to 0 are then put into separate wells followed by 100 μl of a dilution of the alkaline phosphatase conjugate in Tris buffered saline found by similar experimentation to be suitable. The mixtures are incubated overnight at room temperature, the solutions discarded and the wells washed four times with Tris buffered saline. The alkaline phosphatase remaining associated with the wells is then assayed by the addition of 200 μl of a solution of 50 mM bicarbonate buffer pH 10.3 containing 3.3 mM MgC12 to each well followed by measurement of the absorbance change at 405 nm at room temperature. A standard curve of absorbance change against concentration of propranolol is drawn and may be used to determine the concentration of propranolol in unknown samples.

EXAMPLE 6

Determination of Methotrexate 5 mg of purified dihydrofolate reductase is mixed with 100 μg of methotrexate in 5 ml of phosphate buffered normal saline (PBS) and left stirred at room temperature for one hour. It is then emulsified with an equal volume of complete Freunds adjuvant and used to immunise a sheep by intramuscular injection. Two weeks later similar injections are given but this time using incomplete Freunds adjuvant. Two weeks later a final booster injection is given without added adjuvant. Three weeks later antiserum is obtained from the sheep. This is absorbed free of antibody against DHFR alone as follows. An immunoabsorbant is made with 20 mg of DHFR using the 'Insolumer' preparation of Sera-Lab Ltd by following their instructions. 0.25 ml of the antiserum is diluted to 5 ml in PBS and mixed gently with the washed immunoabsorbent for one hour at room temperature. The supernatant is then obtained by centrifugation and filtration through a 0.45μ filter.

Microtitre plates from Nunc are taken and into each well is placed 200 μl if a 10 μg/ml solution of DHFR in 50 mM bicarbonate buffer pH 9.6. The plates are left for four hours at room temperature and then the solutions are shaken out and replaced with 250 μl of a 0.2% solution of ovalbumin in the same bicarbonate buffer. This is again left for four hours at room temperature, shaken out and the plates washed four times with a solution of 50 mM Tris pH 7.4 plus 0.02% Tween 20 (TBT). Standard solutions of methotrexate from 100 μg/ml down to 0 are made in 50 mM Tris pH 7.4 (TB) and 100 μl of each put into separate wells. To these are then added 100 μl of a 1:200 dilution in TB of the supernatant solution obtained after immunoabsorption. The plates are incubated at room temperature for four hours, the solutions shaken out and the plate washed four times with TBT. Anti-sheep IgG antibody conjugated by conventional means employing glutaraldehyde to alkaline phosphatase to be used with enzyme labelled immunoassay systems at 1:1000 dilution was obtained from Guildhay Ltd. It is diluted 1:1000 with TB containing normal saline (TBS) and 200 μl of the diluted conjugate put into each microtitre well and incubated for a further four hours at room temperature. The solutions are then shaken out and the wells washed four times with TBT. 200 μl of a 10 mM solution of para-nitrophenyl phosphate in 50 mM bicarbonate buffer pH 10.3 and containing 3.3 mM MgCl$_2$ is then added to each well and the plate incubated at room temperature. The change in optical density of the contents of the wells at 405 nm is recorded. This is related to the concentration of methotrexate in the particular wells there being an increase in the rate of change of optical density with increasiwng methotrexate concentration over a range of concentration of methotrexate. A standard curve may then be drawn to determine the concentration of methotrexate in unknown samples within this concentration range.

EXAMPLE 7

Determination of Methotrexate

This is carried out as in Example 6, however, the antiserum is fractionated before immunoabsorption to yield an IgG fraction and after the immunoabsorption this is then conjugated by conventional means with glutaraldehyde to form a conjugate with alkaline phosphatase. The degree of dilution required for this conjugate in the assay is determined by trial using a microtitre plate coated with DHFR as above, adding a range of concentrations of methotrexate and the conjugate and conducting an assay as described above. With the optimal dilution of the conjugate determined a standard curve for methotrexate is constructed by taking a DHFR coated plate, adding 100 μl of a range of dilutions of methotrexate as above and 100 μl of the diluted conjugate, incubating for four hours at room temperature and then shaking the solutions out of the wells. The wells are then washed four times with TBT and the remaining phosphatase assayed as above to give rise to a standard curve of methotrexate concentration against optical density change.

EXAMPLE 8

Determination of Folate

This is conducted as Example 6 but this time using purified folate binding protein (FBP) obtained from milk as the binding protein (instead of DHFR) with its small molecule folate. In an analogous fashion a complex of FBP and folate is used to immunise a sheep, the antiserum absorbed free of antibody against FBP alone and then used to construct a standard curve for folate in an anlogious manner to that for methotrexate in Example 2.

I claim:

1. A polyclonal antibody which comprises a secondary antibody against a complex of a hapten of molecular weight less than 5000 and a binding protein against said hapten, said antibody being free from antibodies against the hapten and its binding protein.

2. A polyclonal antibody as claimed in claim 1 which comprises a secondary antibody against a complex of a hapten of molecular weight 200 to 1000 and a primary monoclonal antibody against said hapten, said secondary antibody being free from antibodies against the hapten and its primary monoclonal antibody.

3. A polyclonal antibody according to claim 2 wherein the hapten has a molecular weight of 300 to 600.

4. A polyclonal antibody according to claim 2 which is labelled whereby it is detectable.

5. A polyclonal antibody according to claim 4 wherein the label is either (a) an enzymatic label or (b) a luminescent label.

6. A polyclonal antibody according to claim 4 wherein the label is alkaline phosphatase.

7. A method of determining a member of a specific binding pair of hapten of molecular weight 200 to 1000 and its primary antibody which method comprises contacting a suspected source of a member of the pair with the other member of the pair and with a secondary polyclonal antibody to the complex of the pair which is not an antibody to the hapten or its primary antibody and measuring the association between the complex and the secondary polyclonal antibody and relating said measured association to the amount of said member.

8. A method according to claim 7 for the determination of a hapten of molecular weight 200 to 1000 wherein the secondary polyclonal antibody is labelled.

9. A polyclonal antibody according to claim 1 wherein the hapten is of molecular weight 250 to 750.

10. A polyclonal antibody according to claim 1 which is a complete immunoglobulin.

11. A polyclonal antibody according to claim 1 wherein the antibody is a Fab or F(ab$^1$)$_2$ fragment.

12. A polyclonal antibody according to claim 1 wherein the hapten is a hormone, vitamin, peptide, saccharide, medicament or drug of abuse.

13. A polyclonal antibody according to claim 1 wherein the hapten is estradiol, testosterone, progesterone, hydrocortisol, cortisol, an antibiotic, a mood modifier, an analgesic, morphine, methadone, cannabiniol or a cocaine alkaloid.

14. A polyclonal antibody according to claim 2 which comprises a secondary antibody against a complex of testosterone and a primary antibody against testosterone said secondary antibody being free from antibodies against testosterone and its primary antibody.

15. A polyclonal antibody according to claim 2 wherein the ratio of the equilibrium constants between the secondary polyclonal antibody and the complex and the secondary polyclonal antibody and either component of the complex is greater than 100:1.

16. A polyclonal antibody according to claim 5 wherein the luminescent moiety is a bioluminescent, chemiluminescent or fluorescent material.

17. A method according to claim 7 which comprises a two site assay in which the primary antibody is bound to a surface.

18. A method according to claim 7 wherein the member of a pair to be detected is the hapten.

19. A method according to claim 18 wherein the hapten is a hormone, vitamin, peptide, saccharide, medicament or drug of abuse.

20. A method according to claim 18 wherein the hapten is estradiol, testosterone, progesterone, hydrocortisol, cortisol, an antibiotic, a mood modifier, an analgesic, morphine, methadone, cannabiniol or a cocaine alkaloid.

21. A method according to claim 7 wherein the primary antibody is a monoclonal antibody.

* * * * *